United States Patent [19]

Aviron Violet

[11] 3,949,000
[45] Apr. 6, 1976

[54] ASYMMETRIC DIPHOSPHINES, THEIR PREPARATION AND THEIR USE

[75] Inventor: Paul Aviron Violet, Saint-Genis-Laval, France

[73] Assignee: Rhone-Poulenc S.A., Paris, France

[22] Filed: May 17, 1974

[21] Appl. No.: 470,866

[30] Foreign Application Priority Data
May 21, 1973  France .............................. 73.18319

[52] U.S. Cl. ...................... 260/606.5 P; 252/431 P; 260/326.14 T; 260/340.5; 260/429 R; 260/468 J; 260/471 A; 260/482 R; 260/514 J; 260/518 R; 260/519; 260/534 R
[51] Int. Cl.² .......................................... C07F 9/02
[58] Field of Search ...................... 260/606.5 P

[56] References Cited
UNITED STATES PATENTS
3,798,241  3/1974  Kagan et al. ................ 260/606.5 P FOREIGN PATENTS OR APPLICATIONS
2,116,904  7/1972  France OTHER PUBLICATIONS
Kosolapoff, Organic Phosphorus Compounds, Wiley-Interscience, N.Y. Vol. 1, pp. 202–210 (1972).
Schindlbauer, Monatshefte fur Chemie, Vol. 96, pp. 2058–2060 (1965).
Cotton, Progress In Inorganic Chemistry, Vol. 5, pp. 144–146 (1963).
Emeleus, Adv. In Inorganic Chemistry And Radio—Chemistry, Vol. 14, pp. 240–244 (1972).

Primary Examiner—Helen M. S. Sneed
Attorney, Agent, or Firm—Stevens, Davis, Miller & Mosher

[57] ABSTRACT

Optically active diphosphines of the formula:

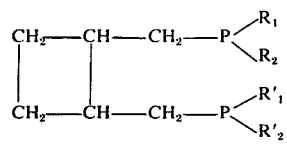

in which the phosphinomethyl groups are trans to each other, form rhodium complexes useful as catalysts in hydrogenating substituted acrylic acids and their esters to optically active propionic acid derivatives.

4 Claims, No Drawings

ASYMMETRIC DIPHOSPHINES, THEIR PREPARATION AND THEIR USE

The present invention relates to asymmetric diphosphines, their preparation and their use.

Asymmetric phosphines and diphosphines are known with which is is possible to produce complexes of transition metals having optically active co-ordinating groups. Such complexes can be used to catalyse the hydrogenation of unsaturated compounds to form saturated compounds having optical activity. Thus French Pat. No. 2,116,905 describes asymmetric diphosphines of the formula:

$$R_2P - R' - PR_2$$

in which R' represents a divalent hydrocarbon radical containing one or more asymmetric carbon atoms and optionally hetero-atoms, and R represents an aliphatic, cycloaliphatic or aromatic hydrocarbon radical. The divalent hydrocarbon radical R' can be alkylene, cycloalkylene or aralkylene radical. These diphosphines can be used to make catalysts with which it is possible to hydrogenate unsaturated compounds to form saturated compounds possessing optical activity, in worthwhile yields. The yield of optical stereoisomer is not however quantitative and it is therefore desirable to increase the selectivity of the reaction. In fact, in many cases the presence of even a relatively small proportion of the opposite optical stereoisomer to that desired can make it necessary to separate the two stereoisomers, particularly for therapeutic use. It is thus important to have a hydrogenation which is as selective as possible, in order to avoid or at least reduce the need to resolve the product optically.

The present invention provides new asymmetric diphosphines which make it possible to make rhodium complexes which catalyse the asymmetric hydrogenation of substituted acrylic acids and their esters which are precursors of aminoacids. The diphosphines of the invention are optically active stereoisomers of the formula:

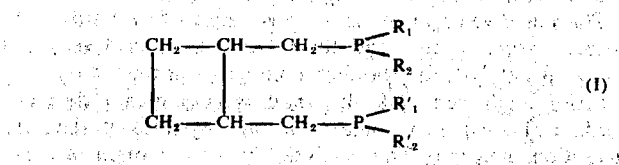

in which the phosphinomethyl groups are situated in the trans position relative to one another and the radicals $R_1$, $R_2$, $R'_1$ and $R'_2$, which may be identical or different, each represent straight or branched alkyl of 1 to 8 carbon atoms, cycloalkyl of 5 to 6 ring carbon atoms, or aryl consisting of one or more benzene rings which are bonded to one another by a valency bond or which form with one another an ortho- or peri-condensed system such as naphthyl, acenaphthyl or phenanthrenyl. These aryl groups can optionally be substituted by straight or branched alkyl of 1 to 4 carbon atoms.

Preferred diphosphines of formula (I) are those in which the radicals $R'_1$ and $R'_2$ are respectively identical to the radicals $R_1$ and $R_2$. These diphosphines are more readily available than the diphosphines carrying 4 different substituents. It is especially preferred that $R_1$, $R_2$, $R'_1$ and $R'_2$ are identical.

Furthermore, the diphosphines of formula (I) in which the radicals $R_1$, $R_2$, $R'_1$ and $R'_2$ represent an aryl group such as phenyl, tolyl, naphthyl, or xylyl form a preferred category of diphosphines which are very suitable for the preparation of rhodium complexes, which are very selective asymmetric hydrogenation catalysts.

By way of illustration of the diphosphines of formula (I) there may be mentioned, those in which the phosphinomethyl group is dimethylphosphinomethyl, dibutylphosphinomethyl, dioctylphosphinomethyl, diphenylphosphinomethyl, dinaphthylphosphinomethyl, ditolylphosphinomethyl or ethylhexylphosphinomethyl.

Using the process for the preparation of the diphosphines described below, it is possible to obtain each stereoisomer of the diphosphines of formula (I). As has already been indicated, each stereisomer forms part of the invention. Mixtures of stereoisomers containing a major proportion of one stereoisomer are also part of the invention. Such mixtures in which the proportion of one stereoisomer is greater than 90% are suitable for effecting the asymmetric hydrogenation of substituted acrylic acids and their esters which are precursors of aminoacids. However, to achieve the best selectivities, it is preferable to use a pure diphosphine stereoisomer.

The diphosphines of formula (I) can be produced by treating a sulphonic acid ester of a stereoisomer of trans-bis-(1,2-hydroxymethyl)-cyclobutane with an alkali metal phosphide of formula $R_1R_2PM$ (M representing an alkali metal). The preferred sulphonic acid esters are the trans-bis(1,2-hydroxymethyl)-cyclobutane ditosylates. This general method for producing phosphines has been described by H. SCHLINDLBAUER [Monatshefte fur Chemie, 96 2058 60 (1965)]. The alkali metal phosphides are, for example, described in Houben-Weyl: [Methoden der Organisch Chemie: Phosphorverbindungen, volume 12/1, p. 23–24].

Resolved trans-bis-(1,2-hydroxymethyl)-cyclobutane ditosylates can be produced by reacting p-toluenesulphonic acid chloride with an optically active trans-bis-(1,2-hydroxymethyl)-cyclobutane in accordance with a process similar to that described by M. CARMACK and C. J. KELLEY [Journal of Organic Chemistry, 2171-3 (1968)].

The stereoisomer of trans-bis-(1,2-hydroxymethyl)-cyclobutane can in their turn be produced by reduction with lithium aluminium hydride, of optically active cyclobutane-trans-1,2-dicarboxylic acid [method described by N. G. GAYLORD; Reduction with Complex metal hydrides, P. 365–373, Inter-Science Publishers (1956)]. The stereoisomers of cyclobutane-trans-1,2-dicarboxylic acid have been described by E. COYNER and W. S. HILLMAN [Journal of the American Chemical Society, 71, 324–6 (1949)].

A further subject of the present invention is the rhodium complexes containing halogen atoms and optionally carbonyl groups, which possess, as ligands, the diphosphines of the invention. These complexes can be produced by reacting an excess of the diphosphine of formula I with hydrated rhodium chloride $RhCl_3 \cdot 3H_2O$, in ethanol, according to a method similar to that described by J. A. OSBORN, F. H. JARDINE, J. F. YOUNG and G. WILKINSON [Journal of Chemical Society, 1711–32 (1966)]. It is also possible to react a rhodium complex previously formed from an unsaturated compound such as a mono- or di- olefine, with a diphosphine of formula I. This is the preferred way of making the chlorinated complexes. Suitable complexes with mono- or di- olefines are the μ-dichlorotetraethylene-rhodium complex [Journal of American Chemical Society, 88, 4537–8 (1966)], and the dichlorohexadiene-rhodium complex [Chemical Communications, 10–11 (1972)]. The amount of diphosphine of formula I employed is usually between 0.5 and 2 mols of diphosphine per rhodium atom present in the complex.

The corresponding iodinated and brominated complexes can be produced readily from the chlorinated complexes. To do this, it is sufficient to react the chlorinated complex with lithium bromide or iodide according to a method similar to that described in Journal of Chemical Society, 1711–32 (1966). It is also possible to convert the chlorinated complexes to carbonyl-containing complexes by the action of carbon monoxide according to the technique described in Journal of Chemical Society, 1711–32 (1966). These complexes also form part of the present invention.

A further feature of the present invention is a process for the asymmetric hydrogenation of substituted acrylic acids and their esters especially those which are precursors of aminoacids, in which the rhodium complexes described above are used in the presence of hydrogen. These complexes are believed to be converted in situ by the action of hydrogen into new complexes which are the catalysts for the hydrogenation reaction.

The term substituted acrylic acids and their esters which are precursors of aminoacids covers all the compounds, the formula of which is derived from that of acrylic acid or its esters, by replacing at most two of the hydrogen atoms carried by the ethylenic carbon atoms in the following way: One of the hydrogen atoms is replaced by an amine group, which may be primary or secondary, and which can be substituted by an acyl group such as acetyl or benzoyl; another of the hydrogen atoms of the ethylenic carbon atoms can be replaced by one of the following groups, namely: a straight or branched alkyl such as methyl, ethyl, isopropyl and isobutyl, a cycloalkyl group such as cyclopentyl and cyclohexyl, an aromatic hydrocarbon group such as phenyl, naphthyl or acenaphthyl, these radicals being unsubstituted or substituted by e.g., one or more hydroxy and alkoxy radicals, or a heterocyclic group containing one or more oxygen, sulphur or nitrogen atoms, such as furyl, pyranyl, benzopyranyl, benzofuranyl, pyrrolyol, pyridyl or indolyol.

Preferred such compounds have the formula:

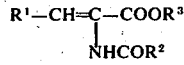

where $R^1$ is alkyl of 1 to 4 carbon atoms, cyclopentyl, cyclohexyl, phenyl, phenyl substituted in the 3- and/or 4- positions by hydroxy, methoxy, ethoxy or methylenedioxy, naphtyl, or 3-indolyl, $R^2$ is hydrogen, alkyl of 1 to 4 carbon atoms, or phenyl, and $R^3$ is hydrogen or alkyl of 1 to 4 carbon atoms.

Examples of such substituted acrylic acids and esters which are precursors of aminoacids are: α-(N-acetylamino)-β-phenyl-acrylic acid and its hydroxyl-containing or alkoxy-containing derivatives, such as the compounds of the formulae:

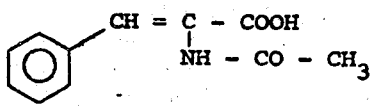

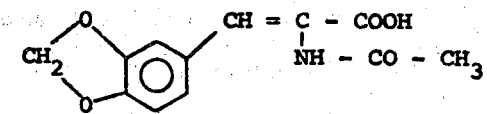

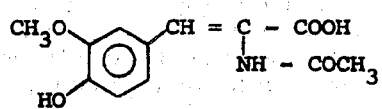

and

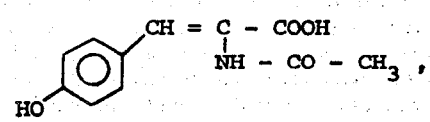

α-(N-benzoyl-amino)-β-phenyl-acrylic acid and its hydroxyl-containing and alkoxy-containing derivatives,
α-(N-acetyl-amino)-β-indolyl-acrylic acid,
α-(N-benzoyl-amino)-β-indolyl-acrylic acid, and
α-(N-acyl-amino)β-isobutyl-acrylic acid.

The selective asymmetric hydrogenation of such substituted acrylic acids and their esters is carried out using, as catalyst, the rhodium complexes produced by reacting hydrogen with the rhodium complexes described above which contain the diphosphines of the invention as ligands. The catalytically active complexes can be prepared directly in situ.

The asymmetric hydrogenation reactions are usually carried out at a temperature of 20 to 100°C, under a partial hydrogen pressure of 0.1 to 50 bars. The amount of rhodium complex employed is generally such that the ratio of the number of rhodium atoms present to the number of mols of compound to be hydrogenated is between 0.1 to 0.000005.

The hydrogenation can be carried out in a hydrocarbon, such as benzene, cyclohexane or toluene, or in a mixture of solvents consisting of a hydrocarbon and an aliphatic alcohol such as ethanol or methanol.

After the hydrogenation complex has been formed, a basic compound can optionally be added. This basic compound can be an alkaline base such as sodium hydroxide or a primary, secondary or tertiary amine (e.g. pyridine, piperidine or triethylamine). The amount of basic compound added is such that the ratio of the number of mols of this compound to the number of rhodium atoms present is between 0 and 25, and preferably between 0 and 12. The presence of the basic compound can help to improve the selectivity of the hydrogenation.

The hydrogenation process of the invention makes it possible to make in improved yields, the various stereoisomers of such amino-acids as phenylalanine, tyrosine (hydroxyphenylalanine), tryptophane (β-indolylalanine), and dopa (dihydroxyphenylalanine).

The examples which follow illustrate the invention.

EXAMPLE 1

A solution consisting of 0.032 mol (13.6 g) of the stereoisomer of trans-bis-(1,2-hydroxymethyl)-cyclobutane ditosylate having an optical rotation $(\alpha)_D = +60.4°$ and 10 cm³ of tetrahydrofuran is run into a solution consisting of 0.065 mol (13.5 g) of sodium diphenylphosphide and 200 cm³ of a 1:1 mixture of dioxane and tetrahydrofuran. After heating under reflux, a precipitate is obtained which is filtered off and washed with benzene. The filtrate is evaporated to dryness and the diphosphine obtained is then recrystallised from absolute ethyl alcohol. Its microanalysis and IR and NMR spectography are in agreement with the formula:

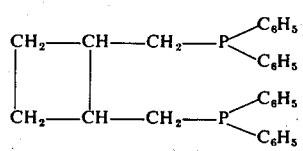

$(\alpha)_D^{20} = -18.5°$ (C = 1% in benzene), melting point = 107°C.

The stereoisomer of trans-bis-(1,2-hydroxymethyl)-cyclobutane was produced by reduction, with lithium aluminium hydride, of (—)-trans-cyclobutanedicarboxylic acid of optical rotation $(\alpha)_D = -155°$.

EXAMPLE 2

Starting from (+)-trans-cyclobutane-1,2-dicarboxylic acid and following the procedure of Example 1, the diphosphine of opposite optical rotation is obtained in substantially identical yield.

EXAMPLE 3

By replacing the sodium diphenylphosphide in the procedure of Example 1 by an identical molar amount of sodium dinaphthylphosphide, the following diphosphine is obtained:

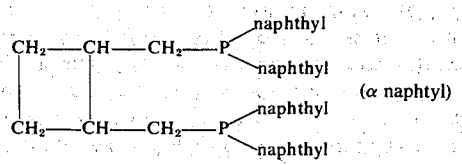

in a yield of 15%, $(\alpha)_D^{22} = 19°$ (C = 0.7% in benzene).

EXAMPLE 4

By replacing the sodium diphenylphosphide in the procedure of Example 1 by an identical molar amount of sodium ditolylphosphide, the following diphosphine is obtained:

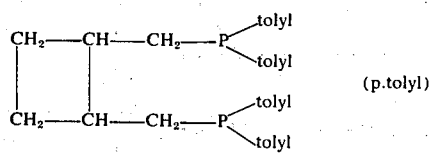

in a yield of 36%, $(\alpha)_D^{22} = 14.5°$ C = 0.7% in benzene).

EXAMPLE 5

The diphosphine prepared in Example 1 is used in the hydrogenation of α-acetamidocinnamic acid.

The catalyst is prepared by adding, under argon, 0.05 mM of the diphosphine prepared as in Example 1 dissolved in 4 cm³ of benzene to a solution of 0.025 mM of the complex of the formula (RhCl-1,5-hexadiene)₂ in 6 cm³ of ethyl alcohol, and stirring the solution for 1 hour. 2.5 mM of α-acetamidocinnamic acid dissolved in 11 cm³ of ethyl alcohol and 4.5 cm³ of benzene are then added, the argon is replaced by hydrogen and hydrogenation is started.

The hydrogenation is complete after ½ hour at 25°C. under a hydrogen pressure of 1 bar. The solution obtained is evaporated to dryness, the residue is taken up in a dilute solution of sodium hydroxide, and the insoluble catalyst is filtered off. The filtrate is acidified and extracted with ethyl acetate. Acetylated phenylalanine is thus obtained in 95% yield and with an $(\alpha)_D^{22}$ of 36.3°.

The optical yield is 70% based on the value $(\alpha)_D^{22} = 51.8$ (ethyl alcohol) for the optically pure product.

EXAMPLE 6

The process of Example 5 is repeated using α-acetamido-β-p-hydroxyphenylacrylic acid as the substitute. The hydrogenation is complete after ½ hour at 25°C under a hydrogen pressure of 1 kg/cm². The solution is evaporated to dryness, the residue is then taken up in water, and the insoluble catalyst is filtered off. After evaporating the filtrate to dryness, acetylated tyrosine with an optical rotation of 41.5° (water) is obtained in 92% yield. The optical yield is 86%.

EXAMPLE 7

The process of Example 5 is added, 0.15 mM of triethylamine being added to the reaction mixture at the same time as the substrate. Acetylated phenylalanine is obtained, after a treatment identical to that of Example 5, in 94% yield and with an $(\alpha)_D^{22} = 42.4°$. The optical yield is 82%.

EXAMPLES 8, 9, 10, 11, 12 and 13

Various substrates are hydrogenated under the working conditions of Example 7 using the rhodium complex prepared as in Example 5 as catalyst. For comparison, the following Table gives the optical yields obtained using, as the rhodium ligand, the following diphosphine, which is described in French Patent No. 2,116,905:

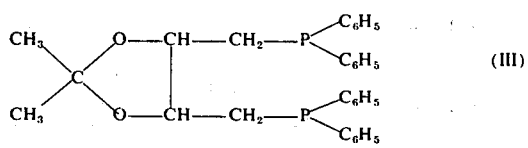

(III)

N-benzoyl-L-tryptophane $(\alpha)_D = -10.4°$ (ethyl alcohol)

The complexes containing the diphosphines of the invention as ligands make it possible to obtain higher optical yields than those obtained from the diphosphine described in French Pat. No. 2,116,905.

EXAMPLE 14

The phenylalanine of the opposite configuration to that obtained in Example 7 is obtained under the conditions of Example 7, by using as the diphosphine that obtained in Example 2. The optical yield is 81%.

EXAMPLE 15

3.1 mg of the complex of the formula [RhCl-1,5-cyclooctadiene]$_2$, 57 mg of the diphosphine of Example 1 and 400 cm$^3$ of ethyl alcohol are introduced under an

TABLE

| Examples | Substrate | Configuration of the optical isomer present in excess | Optical yield % obtained with catalyst of Ex.5 | Optical yield % obtained using the diphosphine complex of French Pat. No. 2116905 |
|---|---|---|---|---|
| 8 | HO-C$_6$H$_4$-CH=C(COOH)(NH-CO-CH$_3$) | R | 87 | 80 |
| 9 | CH$_3$O, HO-C$_6$H$_3$-CH=C(COOH)(NH-CO-CH$_3$) | R | 89 | 79 |
| 10 | CH$_3$O, HO-C$_6$H$_3$-CH=C(COOH)(NH-CO-C$_6$H$_5$) | R | 76 | 63 |
| 11 | CH$_2$O$_2$-C$_6$H$_3$-CH=C(COOH)(NH-CO-CH$_3$) | R | 89 | 76 |
| 12 | indol-3-yl-CH=C(COOH)(NH-CO-CH$_3$) | R | 90 | 67 |
| 13 | indol-3-yl-CH=C(COOH)(NH-CO-C$_6$H$_5$) | R | 70 | 65 |

The optical yields are calculated using the following optical rotations for the optically pure products:
N-acetyl-D-tyrosine $(\alpha)_D = -48.3°$ (water)
N-acetyl-L-(4-hydroxy-3-methoxy-phenyl)-alanine $(\alpha)_D = +42°$ (methyl alcohol)
N-benzoyl-L-(4-hydroxy-3-methoxy-phenyl)-alanine $(\alpha)_D = -32.7°$ (methyl alcohol)
N-acetyl-D-(3,4-methylenedioxy-phenyl)-alanine $(\alpha)_D = -53.4°$ (ethyl alcohol)
N-acetyl-L-tryptophane $(\alpha)_D = +25°$ (95% ethyl alcohol)

argon atmosphere into a reactor. The mixture is stirred for 1 hour. 66.62 g of α-acetamidocinnamic acid and 25 microliters of triethylamine are then added and hydrogen is introduced under a pressure of 1 bar at 25°C. After 4 hours 30 minutes the hydrogenation is complete. After treatment to remove the catalyst similar to that of Example 5, N-acetylphenylalanine is obtained, after extraction, in 97% chemical yield and with an optical rotation $[\alpha]_D^{22}$ of 42.5° (optical yield 82%).

I claim:
1. A stereoisomer of a diphosphine of the formula:

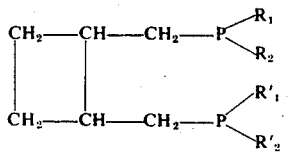

in which the phosphinomethyl groups are in the trans-position relative to one another, and the radicals $R_1$, $R_2$, $R'_1$ and $R'_2$, which may be identical or different, each represent; straight or branched alkyl of 1 to 8 carbon atoms, cycloalkyl of 5 or 6 ring carbon atoms, or aryl consisting of one or more benzene rings which are bonded to one another by a valency bond or which form with one another an ortho- or peri-condensed system, the said aryl being unsubstituted or substituted by straight or branched alkyl of 1 to 4 carbon atoms.

2. A stereoisomer of a diphosphine according to claim 1 in which $R'_1$ and $R'_2$ are respectively identical to the radicals $R_1$ and $R_2$.

3. A stereoisomer of a diphosphine according to claim 2 in which $R_1$, $R_2$, $R'_1$ and $R'_2$ are identical.

4. A stereoisomer of a diphosphine according to claim 1 in which each of $R_1$, $R_2$, $R'_1$ and $R'_2$ is phenyl, tolyl, naphthyl or xylyl.

* * * * *